US008781552B2

United States Patent
Lu et al.

(10) Patent No.: US 8,781,552 B2
(45) Date of Patent: Jul. 15, 2014

(54) LOCALIZATION OF AORTA AND LEFT ATRIUM FROM MAGNETIC RESONANCE IMAGING

(75) Inventors: Xiaoguang Lu, West Windsor, NJ (US); Marie-Pierre Jolly, Hillsborough, NJ (US)

(73) Assignee: Siemens Aktiengesellschaft, Munich (DE)

( * ) Notice: Subject to any disclaimer, the term of this patent is extended or adjusted under 35 U.S.C. 154(b) by 68 days.

(21) Appl. No.: 13/546,101

(22) Filed: Jul. 11, 2012

(65) Prior Publication Data

US 2013/0096414 A1 Apr. 18, 2013

Related U.S. Application Data

(60) Provisional application No. 61/546,156, filed on Oct. 12, 2011.

(51) Int. Cl.
*A61B 5/055* (2006.01)
*G06K 9/00* (2006.01)
*A61B 5/00* (2006.01)
*G01R 33/483* (2006.01)

(52) U.S. Cl.
CPC ............. *A61B 5/055* (2013.01); *A61B 5/0044* (2013.01); *A61B 2576/023* (2013.01); *A61B 5/7267* (2013.01); *G01R 33/483* (2013.01)
USPC .......................................... 600/410; 382/131

(58) Field of Classification Search
USPC ........... 600/410; 382/128, 131, 159, 173, 199
See application file for complete search history.

(56) References Cited

U.S. PATENT DOCUMENTS

| | | | |
|---|---|---|---|
| 7,916,919 B2 | 3/2011 | Zheng et al. | |
| 2003/0035573 A1 | 2/2003 | Duta et al. | |
| 2005/0238215 A1 | 10/2005 | Jolly et al. | |
| 2010/0040272 A1 | 2/2010 | Zheng et al. | |
| 2010/0067764 A1 | 3/2010 | Lu et al. | |
| 2012/0121152 A1 | 5/2012 | Lu et al. | |
| 2013/0083983 A1* | 4/2013 | Zhong et al. | ........... 382/128 |

OTHER PUBLICATIONS

X. Lu, et al., "Automatic Delineation of Left and Right Ventricles in Cardiac MRI Sequences Using a Joint Ventricular Model," Functional Imaging and Modeling of the Heart (FIMH), New York, NY 2011.
Marie-Pierre Jolly, "Automatic Segmentation of the Left Ventricle in Cardiac MR and CT Images," International Journal of Computer Vision, 70(2), pp. 151-163, 2006.
Z. Tu, "Porbabilistic Boosting-Tree: Learning Discriminative Models for Classification, Recognition, and Clustering," Proc. International Conference on Computer Vision, pp. 1589-1596, 2005.
X. Lu, et al., "Cardiac Anchoring in MRI through Context Modeling," Proc. International Conference on Medical Image Computing and Computer Assisted Intervention (MICCAI), LNCS 6361, pp. 383-390, 2010.

* cited by examiner

*Primary Examiner* — Michael Rozanski

(57) ABSTRACT

The aorta and left atrium are localized from magnetic resonance data. The locations of the aorta and left atrium are detected jointly. The aorta and the left atrium are, at least in part, treated as one object. The detection may be from data representing a two-dimensional region. The two-dimensional region may be determined by first detecting the left ventricle from data representing a volume.

20 Claims, 3 Drawing Sheets

LOCALIZATION OF AORTA AND LEFT ATRIUM FROM MAGNETIC RESONANCE IMAGING

RELATED APPLICATIONS

The present patent document claims the benefit of the filing dates under 35 U.S.C. §119(e) of Provisional U.S. Patent Application Ser. No. 61/546,156, filed Oct. 12, 2011, which is hereby incorporated by reference.

BACKGROUND

The present embodiments relate to locating cardiac anatomy. In particular, the aorta and left atrium are located using data representing a patient.

Accurate morphological and functional measurements of the heart assist in clinical applications for diagnosis, prognostic, and therapeutic decisions. In addition to the left ventricle (left ventricle) evaluation during a cardiac exam, aorta and left atrium (LA) evaluation may be important in analyzing the heart functionalities. For example, the aorta is used to measure blood flow, and LA is used to examine electrophysiological behavior. Standard heart views (e.g., 2-chamber, 3-chamber, 4-chamber and short-axis views from base to apex) for diagnosis may be imaged based on position determination of the aorta and/or left atrium.

Magnetic resonance imaging (MRI) allows morphological characterization of heart structures with precision. Cardiac MRI is used in clinical practice due to good image quality and balance of spatial and temporal resolutions over CT and ultrasound. To achieve better image quality, the anatomy of interest is aligned with an iso-center of a MRI scanner.

To locate the heart of the patient to be placed at the iso-center or for subsequent scanning for a standard view, two-dimensional images of the patient are acquired. The heart is anchored using a multi-step approach involving the acquisition of double-oblique slices, such as a stack of slices across the left ventricle long axis (e.g., pseudo short-axis (PSAX) views). Based on these localizer images, the part of the heart is manually anchored. The slice where the anatomy of target resides is selected by the user. The anatomy is anchored by the user with a marker, such as anchoring the left atrium center in the two-dimensional (2D) slice. As these 2D slices have their three-dimensional (3D) world-coordinates recorded, the 3D world-coordinates of the anchor for the target anatomy may be calculated. The entire anchoring process relies on detailed knowledge of the heart for operators and a number of interactions with the scanner user interface to browse the localizer slices and select locations, all while the patient is in the scanner. This approach is operator-dependent and time consuming.

BRIEF SUMMARY

By way of introduction, the preferred embodiments described below include methods, computer readable media and systems for automated localization of the aorta and left atrium from magnetic resonance data. The locations of the aorta and left atrium are detected jointly. The aorta and the left atrium are, at least in part, treated as one object. The detection may be from data representing a two-dimensional region. The two-dimensional region may be determined by first detecting the left ventricle from data representing a volume.

In a first aspect, a method is provided for localization of the aorta and left atrium from magnetic resonance data. A plurality of frames of the magnetic resonance data representing a plurality, respectively, of first planes through a heart of a patient are acquired. A volume of the heart is reconstructed with the frames of the magnetic resonance data. A position of a left ventricle is detected from the magnetic resonance data of the reconstructed volume. A second plane through the heart and the corresponding magnetic resonance data are identified based on the position of the left ventricle. A processor detects, jointly and two-dimensionally, the aorta and the left atrium from the magnetic resonance data for the second plane. An image is displayed as a function of the detecting of the aorta and left atrium.

In a second aspect, a non-transitory computer readable storage medium has stored therein data representing instructions executable by a programmed processor for localization of the aorta and left atrium from magnetic resonance data. The storage medium includes instructions for receiving the magnetic resonance data representing a patient, jointly detecting the aorta and the left atrium from the magnetic resonance data, and determining a location of the aorta and a location of the left atrium from the jointly detecting.

In a third aspect, a system is provided for localization of the aorta and left atrium from magnetic resonance data. A magnetic resonance scanner is configured to acquire magnetic resonance data representing a three-dimensional region of a patient. A processor is configured to detect a left ventricle in the three-dimensional region of the patient from the magnetic resonance data, to detect an object encompassing both the aorta and the left atrium based on the left ventricle, and to localize the aorta and the left atrium from the object.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The aorta and left atrium are automatically localized. The aorta and left atrium are jointly detected from cardiac MRI localizer acquisitions. Learning-based algorithms are applied to the localizer slices to identify cardiac anatomies. Non-learning based algorithms may be used. Localization of cardiac landmarks is used in cardiac MRI to achieve efficient scanning with high accuracies.

In one embodiment, the aorta and left atrium are automatically localized from PSAX slices with a navigated approach. The left ventricle (left ventricle) is localized. The left ventricle has a relative consistent and rather unique shape appearance compared to other heart anatomies. The left ventricle tends to be more distinctive, resulting in better detection accuracies using discriminative approaches. A slice to localize the aorta and left atrium (LA) is determined based on the left ventricle and an anatomical constraint of the heart. For aorta and LA detection, the aorta and LA are treated as a single object to take into account joint context between the aorta and the LA, in addition to each individual context. Instead of localizing each anatomy independently, the joint context constructed by the aorta and LA is analyzed, taking advantage of anatomical constraints between the aorta and the LA in the heart. Non-navigated approaches may be used, such as directly detecting the aorta and LA jointly and without first identifying other anatomy.

Figure 1:
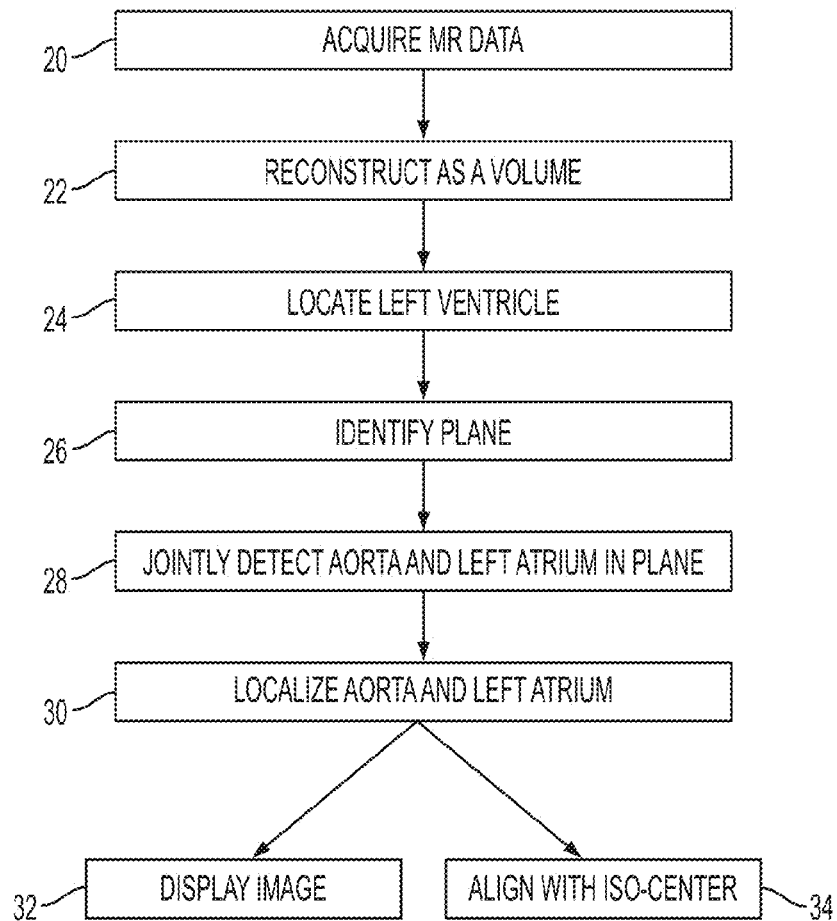
FIG. 1 is a flow chart diagram of one embodiment of a method for localization of the aorta and left atrium from magnetic resonance data.

FIG. 1 shows a method for localization of the aorta and left atrium from magnetic resonance data. The method is implemented by a medical diagnostic imaging system, a review station, a workstation, a computer, a PACS station, a server, combinations thereof, or other device for image processing medical diagnostic data. For example, the system or processor with instructions from computer readable media shown in FIG. 4 or 5 implements the method, but other systems may be used.

The method is implemented in the order shown or a different order. For example, acts 32 and 34 are performed in parallel or sequentially in any order. Additional, different, or fewer acts may be performed. For example, acts 28 and 30 are performed without any one or more (e.g., all) other acts, such as without acts 22, 24, and 26. As another example, acts 32 and/or 34 are not performed. In yet another example, other acts for detecting additional anatomy, integrating the localization with control of the MRI system, and/or use of the detected position or characteristics of the aorta and/or the left atrium are performed.

The acts are performed in real-time, such as during a cardiac or angiographic imaging session. The aorta and left ventricle are detected and localized for use during the imaging session, such as to position the heart or desired portion of the heart for acquiring additional MR data and/or to establish scan planes based on the anchored anatomy. The acts are performed while the patient is within the room with the MR system or within a scanning position in the MR system. In other embodiments, the aorta and left ventricle are localized for other purposes, so the acts may be performed after the scanned patient has left.

The acts are performed automatically by a processor. The user causes the patient to be scanned or obtains scan data for the patient from a previous scan. The user may activate the process. The user may control the scanning, but the processor performs the acts of detecting and localizing. Once activated, the acts 22-30 are performed without user input. User input of locations of the anatomy in any of the scan data may be avoided. Some user input may be provided, such as for changing modeling parameter values, correcting detected locations, and/or to confirm accuracy. In other embodiments, the acts are part of a semi-automated process using various user interactions to localize the anatomy.

In act 20, magnetic resonance (MR) data representing a patient is received. In one embodiment, the MR data is received from a memory (e.g., from a picture archiving and communications system) or by transfer through a network. MR data acquired by scanning a patient in the present or past is loaded or obtained. In an alternative embodiment, the MR data is received from the MR scanner, such as receiving the MR data during an imaging session or while a patient is being scanned.

The MR data represents the patient. Using the MR system, a sequence of radio frequency pulses in controlled magnetic fields is used to generate a response from selected atoms. Any MR sequence may be used. The response is used to generate MR data. The MR data may be k-space or object space data. As image data, the MR data is to be used or has been used for generating an image.

A frame of MR data representing a region at a given time or period is received. The frame of MR data represents a point, line, plane, or volume (e.g., multiple planes) of the patient. Additional frames may be acquired for different times and/or different regions.

In one embodiment, a plurality of frames representing a plurality of different regions is acquired. The different regions are different planes or slices. The planes are through the heart. The planes are parallel, but may be non-parallel. For example, a plurality (e.g., five or more) of parallel double-oblique slices through the heart are scanned with triggering based on the heart cycle. The corresponding frames of MR data may represent a stack of pseudo-short-axis views of the heart. The MR data corresponds to a localizer acquisition for finding anatomy. Other scanning processes may be used.

Figure 3:
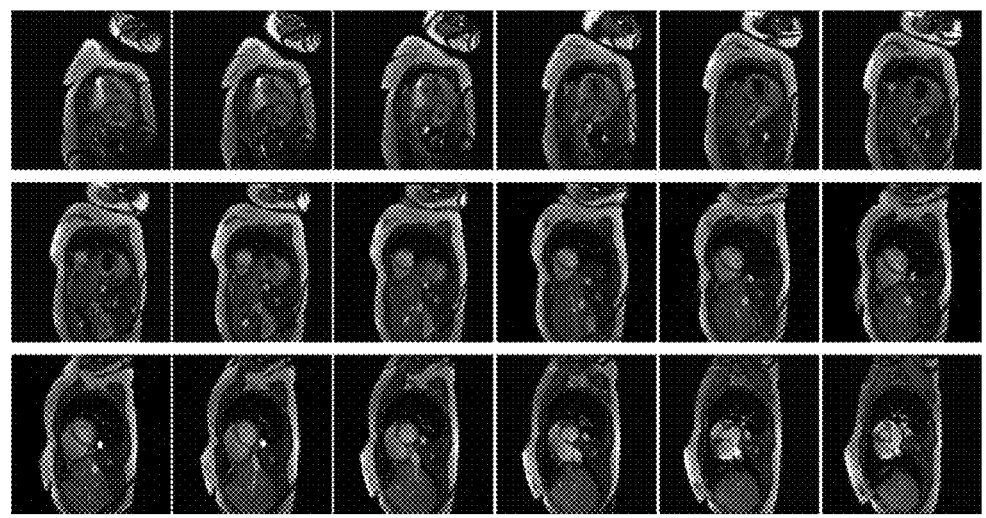
FIG. 3 shows example images acquired as navigation slices.

FIG. 3 shows an example set of eighteen two-dimensional images of pseudo-short-axis (PSAX) slices. The images represent parallel planes and are acquired in a cardiac localizer acquisition. The data of the images, object space data before mapping to display values, or k-space data may be used as the MR data.

In act 22 of FIG. 1, a volume is reconstructed. The volume is reconstructed from the frames of MR data representing different planes through the heart, so is a volume of the heart. For example, the PSAX views are used to form or represent the volume of the heart. The volume is reconstructed from the localizer stack. Volumes including parts or all of other organs may be provided. Volumes not including the heart may be provided.

The volume is formed from MR data representing samples distributed in three-dimensions. A grid of samples is provided. The grid is a regularly spaced rectangular grid in one embodiment. Irregular grids or sampling may be used. Triangular, hexagonal or other type of grid may be used.

The planes represented by the MR data are spatially arranged, such as being stacked based on the MR scan or spatial position recorded during acquisition. The MR data of the stacked frames is interpolated to the three-dimensional grid. Nearest neighbor, bilinear, or trilinear interpolation may be used. In alternative embodiments, the MR data and plane spacing is acquired along the three-dimensional grid. Reconstruction associates the MR data of the planes with the volume. In yet other embodiments, the sampling provided by the MR data and plane spacing is used as the three-dimensional grid without resampling or interpolation.

The MR data of the volume are voxels. A value, such as an intensity, is provided for each voxel. Each voxel represents a point on the grid or a three-dimensional sample region.

Figure 2:
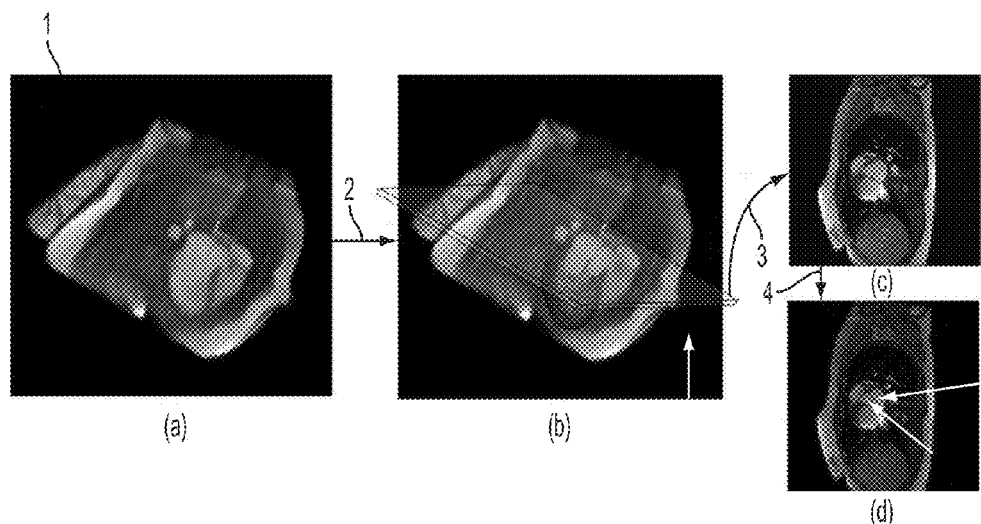
FIG. 2 is an illustration of another embodiment of the method for localization of the aorta and left atrium from magnetic resonance data.

FIG. 2 shows another embodiment of the method for localizing the aorta and the left atrium. In the first stage, the volume is reconstructed as shown in FIG. 2a. FIG. 2a is a three-dimensional rendering of a reconstructed volume.

In act 24, the left ventricle is detected in the volume. The position of the left ventricle is determined from the MR data of the reconstructed volume. The position may be a point, line, area, surface, or volume associated with the left ventricle. For example, the location of the heart wall or edge of the blood pool surfaces is detected. As another example, a base of the left ventricle and a long axis are detected. The base, long axis, long axis direction, and/or other characteristic may be derived from detected features, such as detecting the surface from the MR data and calculating the base and long axis from the detected surface. Alternatively, the base, long axis, or other characteristic is detected directly.

Any detection may be used. A template or pattern may be matched to the MR data of the volume. Edge detection may be performed, such as filtering gradients derived from the MR data. Region growing and/or skeletonization may be used.

In one embodiment, a machine-trained classifier is used to detect the left ventricle. To train, MR data for the heart volume from different patients and respective annotations of the left ventricle or characteristic of the left ventricle (i.e., ground truth) is obtained. The training data is processed into a desired set of input features, such as calculating Haar, steerable, or other features. Based on the input features and the annotations, the set of features best distinguishing the left ventricle or left ventricle characteristic (e.g., center of the base plane and long axis direction or surface) from the background are learned. A matrix or function results from the training. The matrix or function determines the desired information (e.g., location of the left ventricle) from an input volume of MR data based on the input features.

Any now known or later developed machine learning approach may be used. For example, a cascaded and hierarchal classifier is used. The translation or general position is found, then the rotation or orientation, and then the scale or size. Some example approaches for localizing the left ventricle using a machine trained algorithm or other approach include those disclosed in U.S. Published Patent Application Nos. 2010/0040272, 2012/0121152, 2005/0238215, and 2003/0035573, and U.S. Pat. No. 7,916,919. Any segmentation of the left ventricle may be used.

In one approach, a mesh representation of the anatomical shape of the left ventricle is generated using a database of 3D training volumes that are manually annotated. Segmentation of the left ventricle by fitting the mesh to the 3D MRI volume may be performed in two stages. First, the left ventricle pose (i.e., position, orientation, and scale) is estimated in the 3D MRI volume at a left ventricle localization stage. A series of learned-based detectors are trained in order to perform the left ventricle pose estimation in a series of marginal spaces with increasing dimensionality. The classifiers are incrementally learned in the series of marginal spaces. The 3D left ventricle pose detection is split into three stages: position (translation) estimation, position-orientation estimation, and position-orientation-scale estimation. A separate detector is trained based on the annotated training volumes for each of these stages. Multiple hypotheses are maintained between the stages, which removes false positives at earlier stages while propagating the correct hypotheses to the final stage. As the dimensionality increases, the valid space region becomes more restricted by previous marginal space classifiers. One hypothesis is selected as the final detection result. This left ventricle localization stage results in an estimated transformation (position, orientation, and scale) of the object, and a mean shape of the left ventricle (i.e., the left ventricle model generated based on the training volumes) is aligned with the 3D volume using the estimated transformation.

The series of the detectors used to estimate the left ventricle pose and extract the left ventricle boundaries may be constructed using probabilistic boosting trees (PBT), which select from a large pool of features a set of discriminative features that are used to distinguish the positive and negative samples. Such a classifier is a tree-based structure which calculates the posterior probability of the presence of the object of interest from the given data. The nodes in the tree are constructed by a non-linear combination of simple classifiers using boosting techniques. For the detector at the translation (position) stage, 3D Haar wavelet-like features, which are calculated efficiently using integral image-based techniques, may be used. For the detectors at the position-orientation and the position-orientation-scale stages, steerable features may be used, whose computation does not require volume rotation and re-scaling. The boundary detectors may also use steerable features.

Then, at a delineation stage, local deformations of the left ventricle model with the estimated pose are applied in order to fit the model to left ventricle boundaries in the 3D MRI volume. Once the left ventricle model pose is estimated in the 3D MRI volume, the mean shape (i.e., average left ventricle model of all of the annotated training volumes) is aligned with the 3D MRI volume using the estimated left ventricle pose to generate an initial estimate of the object shape in the 3D MRI volume. In order to capture the true anatomical morphology of the left ventricle shape, the left ventricle model is deformed by searching the boundary for each vertex of the left ventricle mesh model. The boundary hypotheses are taken along the normal directions at each vertex of the mean model. Detection is achieved using a boundary detector trained using a PBT with steerable features. The detected boundary points are constrained by projecting the detected model onto a shape subspace constructed based on the annotated datasets using principal component analysis. As a result, the mesh model of the left ventricle is fit to the 3D MRI volume to segment the left ventricle.

In another example approach for segmenting the left ventricle, a myocardium contour is determined according to a graph cut of candidate endocardium contours, and a spline is fit to candidate epicardium contours in the absence of shape propagation. A plurality of shape constraints are applied to candidate endocardium contours and candidate epicardium contours to determine the myocardium contour. A template is determined by shape propagation of a plurality of images in a sequence, including the image of interest in the presence of shape propagation.

Referring to FIG. 2, the detected left ventricle from the volume of FIG. 2a is shown in FIG. 2b. In the second stage, a mesh or other boundary representation of the left ventricle is determined.

Referring to FIG. 1, a plane is identified in act 26. The plane is a slice through the heart. The plane defines the MR data to be used for detection of the aorta and the left atrium.

The plane is identified based on the position of the left ventricle. The plane is defined relative to the left ventricle. Anatomical statistics are used to determine the plane position relative to the left ventricle. Given a patient population, the position of the plane most likely to represent the aorta and the left atrium relative to the left ventricle is used. Alternatively, the position of the plane is detected, such as with a machine learned or template approach. The search space, initial position, or other characteristic of the identification of the plane is based on the left ventricle.

Any left ventricle feature may be used to define the plane, such as an axis, a valve, a largest area, an apex, curvature, or a center. In one embodiment, the plane is oriented normal to the long axis direction of the left ventricle. The plane is positioned along the long axis direction based on a distance from the left ventricle base. The distance is predetermined, such as based on anatomical statistics, or is detected from the MR data. In one example, the plane is about 10 mm from the center of the left ventricle base.

The plane is of any orientation relative to the planes of the acquired MR data. Since the volume is reconstructed, arbitrary plane positions may be provided. The plane may or may not be one of the planes for which MR data was acquired. Since the MR data is acquired for pseudo-short-axis views, the plane identified from the left ventricle detection may be one of the scan planes.

In alternative embodiments, the plane is identified without detection of the left ventricle. The user may manually identify the image with the desired view of the both the aorta and the left atrium. A processor may identify the frame of MR data representing both the aorta and the left atrium.

FIG. 2b shows an example plane position relative to the detected left ventricle. In the third stage, the MR data for the two-dimensional plane is extracted, as shown in FIG. 2c. Nearest neighbor, bilinear, or trilinear interpolation are used to extract the MR data for the identified plane.

In act 28 of FIG. 1, the aorta and the left atrium are detected. The detection is from the MR data for the plane identified in act 26. The MR data for the plane is analyzed to locate the aorta and the left atrium. The detection is performed using MR data distributed in two dimensions. In alternative embodiments, the volume rather than a plane is used. A subset of the volume based on the left ventricle location may be used.

The detection is joint. The aorta and left atrium are detected as a single object or separate objects related to each other by one or more constraints (e.g., spring or elastic function). For example, the aorta and left atrium are detected as a single virtual object using a bounding box encompassing or surrounding both anatomical structures. The placement of the bounding box in the two-dimensional region or identified plane is determined as an object detection task. The bounding box defines a joint context for the aorta and the left atrium. The bounding box accounts for individual anatomy as well since the individual anatomy is surrounded by the bounding box. By surrounding both the aorta and the left atrium, the joint context is also accounted for in detection. Separate detectors for the individual anatomy may be used with a joint detector. More context may enhance the discriminative power of the models used for object detection.

The bounding box has any shape. For example, the bounding box may be two separate regions associated with typical aorta and left atrium shapes. As another example, the bounding box is one region with any shape, such as elliptical, circular, rectangular or square.

The detection positions the bounding box on the plane. The characteristics of the box may be a function of the detected aorta and left atrium. For example, the bounding box is square. The square is centered at a middle point between the aorta and the left atrium. The orientation of the square has an axis extending from a left atrium center to an aorta center in the plane. The size or scale of the square is based on a distance from the left atrium center to the aorta center, such as being 1.5 times longer than the distance. Where a square box is used, the bounding box is isotropic in scale.

Any type of detection may be used, such as image processing. In one embedment, a machine-trained detector is used. The machine-trained detector is a joint detector. The machine-learnt classifier is trained before estimation of the model for a given patient, such as days, weeks, months, or years before.

A set of training data from different patients is acquired. The training data is the same type (e.g., MR data) and for the same or similar region (e.g., planar region defined based on the left ventricle) as the data used for any given patient. The training data is filtered or processed to obtain input features for the training or the training data itself is used as the input feature. Example input features for training include Haar and/or steerable features. A large pool of features may be extracted. The large pool is determined by a programmer or may include features systematically determined. The training determines the most determinative features for a given classification and discards lesser or non-determinative features.

To prepare the set of training samples, actual landmarks and/or surfaces in a number of images are manually annotated or indicated for use as a ground truth. Any number of expert annotated frames of data is used.

The detector is trained from the training data set using a computer. A data-driven, learning-based algorithm is applied to the training data. Using machine learning, the classifier is trained. The machine-trained classifier is any one or more classifiers. The classifier may be a model or detector using image processing, filtering, or other techniques. A single class or binary classifier, collection of different classifiers, cascaded classifiers, hierarchal classifier, multi-class classifier, model-based classifier, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

Only one classifier is applied to detect the aorta and left atrium. Alternatively, a series of classifiers are applied. A hierarchal or cascaded approach may be used, such as learning to detect different aspects of the landmarks. The detector may be trained to detect groups or joint model parameters from detected individual possibilities. The joint context associated with possible groups of landmarks, surface, nodes, meshes or other parameters may be used. The individual classifier, joint classifier, or both classifiers use a machine-learnt model or models.

In one embodiment, the machine-trained classifier is a probabilistic boosting tree classifier. The detector is a tree-based structure with which the posterior probabilities of the presence of the aorta and left atrium are calculated from given data. Each detector not only provides a binary decision for a given sample, but also a confidence value (e.g., score) associated with the decision. The nodes in the tree are constructed by a nonlinear combination of simple classifiers using boosting techniques. For example, the classifier has three levels with 40 weak classifiers at each node. The probabilistic boosting tree (PBT) unifies classification, recognition, and clustering into one treatment. Alternatively, a programmed, knowledge based, or other classifier without machine learning is used.

Once trained, a matrix is output. The matrix represents the learnt algorithm for detection from the MR data. For application, the MR data for a plane identified from a specific patient and/or features derived from the MR data are input to the matrix. As an output, the matrix indicates the parameters of the bounding box, such as position, orientation and scale. The output may also include probabilistic information, such as associated with alternative candidates for the location.

In one embodiment, the machine-trained detector is a discriminative model. The discriminative model differentiates between a true landmark set (e.g., aorta and LA centers) and false/mis-located landmark sets. A probabilistic boosting tree (PBT) is used as the detector. The classifier is a tree-based structure with which the posterior probabilities of the presence of the object of interest are calculated from given data.

Context-based landmark detection is used to estimate a parameter set θ of each anatomic landmark in the received medical MR data. In one example, five parameters for each anatomic landmark context include two position parameters (x, y), one orientation parameter (φ), and two scale parameters (sx, sy). Because exhaustively searching in the five-dimensional space is expensive for online applications, marginal space learning (MSL) is used in training a series of detectors (classifiers) to detect these parameters for each anatomic landmark. For each learning/classification task, a probabilistic boosting tree (PBT) is used as the classifier. Each trained classifier is a tree-based structure with which the posterior probabilities of the presence of the landmark of interest are calculated from the candidate context in the MR data. Following the MSL strategy, for each landmark detector, a series of classifiers estimate the parameters at a number of sequential stages in order of complexity, such as translation (position), orientation, and scale. Different stages utilize features calculated from the MR data. Multiple hypotheses are maintained between stages, which remove false positives from earlier stages while propagating correct hypotheses to the final stage. At the end of the final stage, candidates with high probabilities are selected as the candidates for the particular anatomic landmark.

A joint context is constructed for each possible combination of the landmarks. The joint context of multiple landmarks uses a mapping to combine the individual contexts of the landmarks. The mapping may be determined by generating a model that relates the landmarks based on annotated training data. A joint context operator C is defined to represent the context of an object O, whose parameters are represented by θ(i.e., C(O|θ). The operator C is applied to extract features (context information) from contextual appearance. For example, a series of Haar wavelet-like features or steerable features are computed and selected by C. Joint context is defined as context across a set of landmarks. For two objects $O_1$ and $O_2$, which are represented by their respective parameters $\theta_1$ and $\theta_2$, the joint context (JC) is defined as:

$$JC = C(f(\theta_1 \text{ and } \theta_2)). \qquad (1)$$

JC is represented as appearance and encodes the shape by calculating a geometric relationship through a mapping of the bounding box.

The best combination of landmark candidates is determined using a trained joint context detector. The trained joint context classifier is trained based on the joint context of the annotated training images. The joint context detector computes the posterior probability of the joint context hypothesis that is determined by its parameter set (e.g., positions, orientation, and scales). The best combination of anatomic landmark candidates may be determined based on a fusion of information of the probability determined by the joint context detector, and the probabilities determined by each individual landmark detector.

In act 30, the location of the aorta and the location of the left atrium are determined. The location is of a point, line, or area associated with the object. For example, the center, outer edge, or area in the plane of the aorta and/or left atrium is determined. The same or different characteristics for the aorta and left atrium may be determined. For example, the center of the aorta and the center of the left atrium are located.

The output of the detection may be the desired location. The result of the detection is the location. In other embodiments, the locations are derived from the output of the detection. For example, the location of the aorta and the left atrium are inferred from the location of the detected bounding box. The mapping between the bounding box and the anatomical centers is bijective. Once the bounding box is detected, corresponding anatomical centers are inferred with the inverse mapping.

FIG. 2d shows a fourth stage. In the fourth stage, the locations of the aorta and left atrium are determined. The white arrows end at points determined as the centers of the aorta and the left atrium.

In act 32, an image is generated. The image is generated from the previously or subsequently acquired MR data. For example, a two-dimensional image of the identified plane is generated. Any type of image may be generated. For example, the image is three-dimensionally rendered from the volume. Using a user or processor selected point of view with or without a lighting model, the MR data representing the volume is rendered to a two-dimensional display. Any volume rendering may be used, such as projection or surface rendering. In another example, a planar reconstruction is generated from the ultrasound data. A user or processor placed slice or image plane is positioned relative to the volume. The ultrasound data representing or interpolated to represent the plane is used to generate the two-dimensional image. For multi-planar reconstruction, multiple planes are defined through the volume. An image is generated for each plane. In the heart example, the multiple planes may correspond to standard heart views that are generally orthogonal to each other. In alternative or additional embodiments, the image is of text, a graph or other illustration.

The image is generated as a function of the detection of the aorta and the left atrium. In the example of FIG. 2d, the image is of the plane with the locations highlighted. The MR data used to detect the landmarks is used to generate an image for confirmation of the detection. In other embodiments, the locations are used to define imaging plane locations, such as standard heart views. The MR data associated with the standard view is extracted, and an image is generated. In another example, settings for MR scanning associated with the detected locations are displayed for planning further imaging (e.g., new MR data is acquired by scanning along the planes associated with the standard views). In yet another example, a quantity is calculated using the location or locations (e.g., a left atrium volume is determined starting with the left atrium center location as a seed). A volume, area, length, or other quantity is calculated from the MR data. For example, a value representing operation or other characteristic of the aorta is calculated using the location.

Different types of images may be displayed separately or together, such as an MR image of a plane with the locations highlighted and text indicating a value of a quantity derived from the location.

In act 34, the anchoring is used for further MR scanning. The located landmarks may be used to anchor further imaging. The determined locations are used to position the patient. For example, the user may be positioned within the MR system so that one or both of the aorta and/or left atrium points are generally at the iso-center. Generally accounts for magnetic, control, and mechanical tolerances. The positioning of the patient aligns the patient with the iso-center for detailed imaging.

Figure 4:
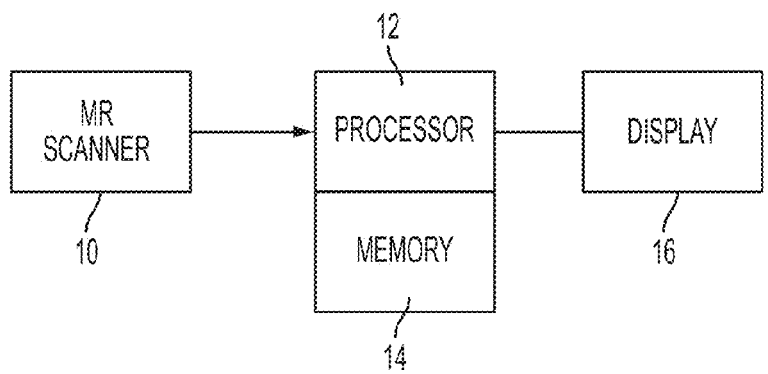
FIG. 4 is a block diagram of one embodiment of a system for localization of the aorta and left atrium from magnetic resonance data.

FIG. 4 shows a system for localization of the aorta and left atrium from magnetic resonance data. The system includes a MR scanner 10, a processor 12, a memory 14, and a display 16. The processor 12 and the memory 14 are shown separately, such associated with being a computer or workstation apart from the MR scanner 10. In other embodiments, the processor 12 and/or memory 14 are part of the MR scanner 10. In alternative embodiments, the system is a workstation, computer, or server using MR data acquired by a separate system in real-time or using previously acquired patient-specific MR data stored in a memory. For example, an MR scanner 10 is provided for acquiring MR data representing a volume or a plurality of planes, and a separate database, server, workstation, and/or computer is provided for creating a model, detecting anatomy, and/or using the location of detected anatomy. Additional, different, or fewer components may be used.

The computing components of the system, such as the MR scanner 10 and/or the processor 12 are configured by hardware, software, and/or design to perform calculations or other acts. The computing components operate independently or in conjunction with each other to perform any given act. The act is performed by one of the computer components, another of the computing components, or a combination of the computing components. Other components may be used by the computing components to scan or perform other functions.

The MR scanner 10 is configured to acquire MR data representing a patient. The MR data is acquired for a three-dimensional region of the patient, such as by scanning a plurality of planes bisecting the heart.

Figure 5:
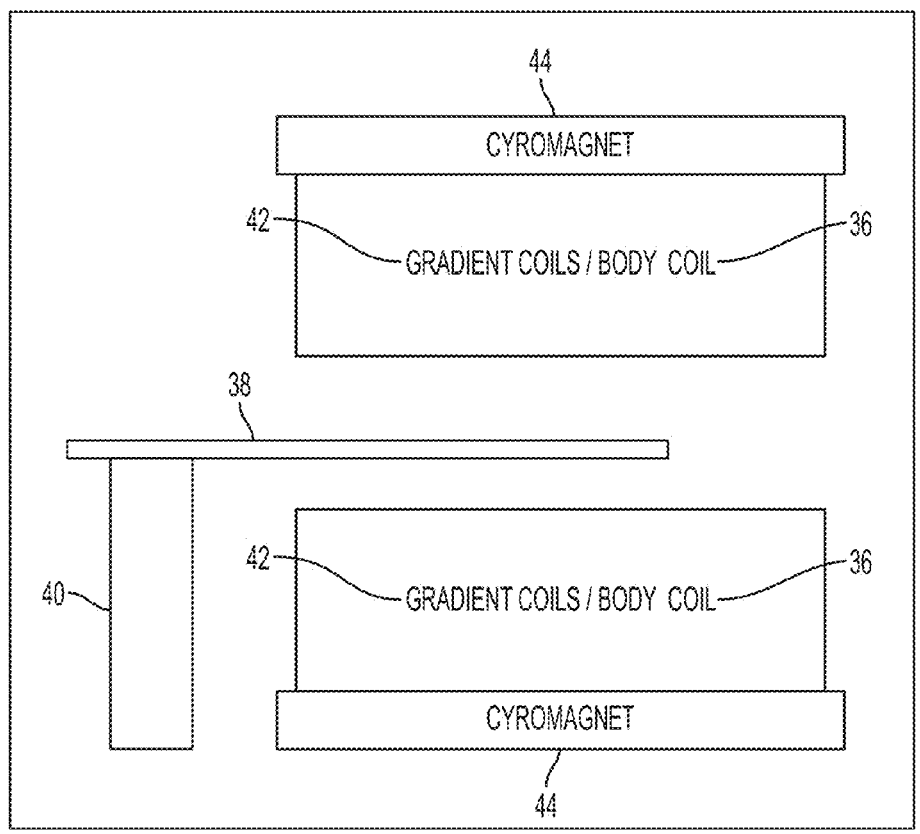
FIG. 5 is a block diagram of one embodiment of a MRI system for localization of the aorta and left atrium from magnetic resonance data.

FIG. 5 shows one embodiment of the MR scanner 10. The magnetic resonance (MR) system includes a cyromagnet 44, gradient coil 42, and body coil 36 in an RF cabin, such as a room isolated by a Faraday cage. A tubular or laterally open examination subject bore encloses a field of view. The isocenter of the cyromagnet 44 is within the bore. A more open arrangement may be provided.

A patient bed 38 (e.g., a patient gurney or table) supports an examination subject, such as a patient with or without one or more local coils. The patient bed 38 may be moved into the examination subject bore in order to generate images of the patient. A robot or support 40 moves the patient bed 38. The patient may be moved in any number of degrees of freedom, such as along a central axis of the bore and up and down.

Other parts of the MR system are provided within a same housing, within a same room (e.g., within the radio frequency (RF) cabin), within a same facility, or connected remotely. The other parts of the MR system may include local coils, cooling systems, pulse generation systems, image processing systems, and user interface systems. Any now known or later developed MR imaging system may be used. The location of the different components of the MR system is within or outside the RF cabin, such as the image processing, tomography, power generation, and user interface components being outside the RF cabin. Power cables, cooling lines, and communication cables connect the pulse generation, magnet control, and detection systems within the RF cabin with the components outside the RF cabin through a filter plate.

The MR system is configured by software, hardware, or both to acquire data representing a plane or volume in the patient. In order to examine the patient, different magnetic fields are temporally and spatially coordinated with one another for application to the patient. The cyromagnet 44 generates a strong static main magnetic field $B_0$ in the range of, for example, 0.2 Tesla to 3 Tesla or more. The main magnetic field $B_0$ is approximately homogeneous in the field of view.

The nuclear spins of atomic nuclei of the patient are excited via magnetic radio-frequency excitation pulses that are transmitted via a radio-frequency antenna, such as a whole body coil 36 and/or a local coil. Radio-frequency excitation pulses are generated, for example, by a pulse generation unit controlled by a pulse sequence control unit. After being amplified using a radio-frequency amplifier, the radio-frequency excitation pulses are routed to the body coil 36 and/or local coils. The body coil 36 is a single-part or includes multiple coils. The signals are at a given frequency band. For example, the MR frequency for a 3 Tesla system is about 123 MHz+/−500 KHz. Different center frequencies and/or bandwidths may be used.

The gradient coils 42 radiate magnetic gradient fields in the course of a measurement in order to produce selective layer excitation and for spatial encoding of the measurement signal. The gradient coils 42 are controlled by a gradient coil control unit that, like the pulse generation unit, is connected to the pulse sequence control unit.

The signals emitted by the excited nuclear spins are received by the local coil and/or body coil 36. In some MR tomography procedures, images having a high signal-to-noise ratio (SNR) may be recorded using local coil arrangements (e.g., loops, local coils). The local coil arrangements (e.g., antenna systems) are disposed in the immediate vicinity of the examination subject on (anterior), under (posterior), or in the patient. The received signals are amplified by associated radio-frequency preamplifiers, transmitted in analog or digitized form, and processed further and digitized by the MR receiver. Received signals may be transmitted by the local coil arrangement to the MR receiver via, for example, coaxial cable or radio link (e.g., via antennas) for localization.

The recorded measured data is stored in digitized form as complex numeric values in a k-space matrix. A one or multi-dimensional Fourier transform reconstructs the object or patient space from the k-space matrix data. The processor 12 or another device performs the reconstruction.

Referring to FIG. 4, the MR system 10 may be configured to acquire different types of data. For example, the MR data represents the anatomy of the patient. The MR data represents the response to the magnetic fields and radio-frequency pulses of tissue. Any tissue may be represented, such as soft tissue, bone, or blood. The MR system 10 may be configured for acquiring specialized functional or anatomic information. For example, T1-weighted, diffusion, thermometry, or T2-weighted MR data is acquired.

The memory 14 stores the MR data representing the patient. Other data may be stored, such as location information, bounding box information, or output images. The MR data represents one or more planes and/or a three-dimensional region. Any format may be used, such as voxels interpolated to a three-dimensional grid, data representing parallel or non-parallel planes in an acquisition format, or data in an imaging format.

The memory 14 is additionally or alternatively a non-transitory computer readable storage medium with processing instructions. The memory 14 stores data representing instructions executable by the programmed processor 12 for localizing the aorta and left atrium. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multi-processing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, three-dimensional data processor, graphics processing unit, application specific integrated circuit, field programmable gate array, digital circuit, analog circuit, combinations thereof, or other now known or later developed device for processing medical data. The processor 12 is a single device, a plurality of devices, or a network. For more than one device, parallel or sequential division of processing may be used. Different devices making up the processor 12 may perform different functions, such as an automated anatomy detector and a separate device for performing measurements associated with the detected anatomy or controlling scanning of standard views based on the detected anatomy. In one embodiment, the processor 12 is a control processor or other processor of the MR system 10. The processor 12 operates pursuant to stored instructions to perform various acts described herein.

The processor 12 is configured to detect a left ventricle from data representing a three-dimensional region of the patient. Any part or the entire left ventricle is detected, such as detecting a left ventricle base and a long axis direction of the left ventricle in the three-dimensional region.

The processor 12 is configured to obtain MR data for a planar region. The planar region is positioned relative to the detected left ventricle, such as a plane normal to the long axis direction and spaced from the center of the left ventricle base by an amount likely to place the plane to intersect both the aorta and the left atrium. The data is obtained by loading from memory based on the plane or causing a further scan of the plane.

The processor 12 is configured to detect an object encompassing both the aorta and the left atrium. The aorta and left atrium are or are not also detected individually. Using a constraint or joint context, the aorta and left atrium are jointly detected. The detection of each influences the detection of the other. Using a bounding box as the object, the bounding box with an orientation, size, and/or position based on the aorta and the left atrium is detected. The detection localizes the aorta and the left atrium, such as calculating the locations from the detected object.

The processor 12 is configured to apply one or more machine trained detectors. For example, the left ventricle is detected with a machine trained detector. As another example, the aorta and left atrium are jointly detected with a machine trained detector. The machine-trained detector outputs one or more locations, such as detecting a surface of the left ventricle, a base center of the left ventricle, a direction of an axis, a center of an aorta in a plane, a center of the left atrium in a plane, or combinations thereof.

The processor 12 may perform machine learning and/or applies a machine-learnt algorithm. For example, the processor 12 applies a probabilistic model to detect anatomy. The probabilistic model is a machine-learned classifier. Any classifier may be applied, such as a model-based classifier or a learned classifier (e.g., classifier based on machine learning). For learned classifiers, binary or multi-class classifiers may be used, such as Bayesian or neural network classifiers. The classifier is instructions, a matrix, a learned code, or other software and/or hardware for distinguishing between information in a medical image.

The classifier may include a plurality of models or classifiers (e.g., detectors) operable together or independently. For example, different probabilistic models are trained for different anatomy. The probabilistic models may be joint or dependent. The location of other anatomies is used to limit or define a search space for a current anatomy and/or as a feature input for classification of another anatomy.

The same or different types of classifiers may be used for the same type of classification, such as different types of classifiers being used for different marginal space classification (e.g., the classifier for finding a region is different than the classifier for landmark and/or surface location determination within the region).

In one embodiment, the probabilistic model is formed from a plurality of probabilistic boosting tree classifiers. Separate training and resulting machine-trained classifiers are provided for each type of landmark and/or surface of interest. For each of these separate classifiers, separate probabilistic boosting tree classifiers are provided for each of the marginal space types. For example, the classifiers follow the marginal space learning protocol.

For application, the processor 12 calculates features for classification. The same or different features are used for classification in each stage of detection. Any features may be used. Different types of features may be used for the same classifier, or all of the features are of a same type for a given classifier. In one embodiment, Haar wavelet-like and/or steerable features are calculated. Haar wavelet-like features represent the difference between different portions of a region. Any number of features may be used, such as tens, hundreds, or thousands. The machine learning process may operate to determine a desired subset or set of features to be used for a given classification task. In one embodiment, the type of features used is gradient features. For example, the steerable features are used. Other types of features may alternatively or additionally be used.

The processor 12 is configured to control the MR scanner 10 and/or move the moveable patient bed. The robot or support 40 is controlled to position the patient relative to the iso-center of the MR scanner 10. The localized aorta, localized left atrium, or both are positioned to be at the iso-center. The MR scanner 10 is controlled to scan planes associated with standard cardiac views based on the locations for the heart anatomy.

The processor 12 is configured to generate an image. The image is generated as a function of the MR data used for position detection. For example, images associated with one or more stages of processing to localize anatomy are displayed. Alternatively or additionally, the localized anatomy is used to determine scan position of the patient and/or scan planes, and images acquired after this subsequent scanning are generated. The image is a two-dimensional image, but may additionally or alternatively be a volume or three-dimensional rendering.

The display 16 is a CRT, LCD, plasma, projector, printer, or other output device for showing an image. The display 16 displays an image of the heart of the patient. The image is an MR image. A value of a measurement may be displayed. The value may be displayed in a chart, graph, and/or on an anatomy image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for localization of the aorta and left atrium from magnetic resonance data, the method comprising:
acquiring a plurality of frames of the magnetic resonance data representing a plurality, respectively, of first planes through a heart of a patient;
reconstructing a volume of the heart with the frames of the magnetic resonance data;
detecting a position of a left ventricle from the magnetic resonance data of the reconstructed volume;
identifying a second plane through the heart and the corresponding magnetic resonance data based on the position of the left ventricle;
detecting, jointly and two-dimensionally with a processor, the aorta and the left atrium from the magnetic resonance data for the second plane; and
displaying an image as a function of the detecting of the aorta and left atrium.

2. The method of claim 1 wherein acquiring comprises acquiring with a localizer acquisition of the magnetic resonance data with the first planes comprising pseudo-short axis views.

3. The method of claim 1 wherein reconstructing the volume comprises interpolating the magnetic resonance data to a three-dimensional, regularly spaced grid for the volume.

4. The method of claim 1 wherein detecting the position of the left ventricle comprises detecting a left ventricle base and a long axis direction.

5. The method of claim 4 wherein identifying the second plane comprises identifying the second plane as normal to the long axis direction and a predetermined distance from the left ventricle base.

6. The method of claim 1 wherein identifying the second plane comprises identifying one of the first planes.

7. The method of claim 1 wherein detecting the aorta and the left atrium comprises detecting with a machine-trained joint detector.

8. The method of claim 7 wherein detecting with the machine-trained joint detector comprises detecting with a probabilistic boosting tree classifier having a tree-based structure.

9. The method of claim 1 wherein detecting the aorta and the left atrium comprises detecting with a bounding box defining a joint context for the aorta and the left atrium.

10. The method of claim 9 wherein detecting with the bounding box comprises detecting with a center of the bounding box being a middle point between the aorta and the left atrium, an orientation of the bounding box being an orientation from a left atrium center to an aorta center in the second plane, and a scale of the bounding box being based on a distance from the left atrium center to the aorta center.

11. The method of claim 10 wherein detecting the aorta and the left atrium comprises detecting a placement of the bounding box in the second plane, and inferring the left atrium center and the aorta center from the bounding box.

12. The method of claim 10 wherein displaying comprises displaying a magnetic resonance image with the aorta and left atrium highlighted, displaying a quantity calculated from locations of the aorta and/or the left atrium, or both.

13. The method of claim 10 further comprising:
aligning the patient with an iso-center of a magnetic resonance scanner, the aligning being a function of a location of the aorta, a location of the left atrium, or both.

14. In a non-transitory computer readable storage medium having stored therein data representing instructions executable by a programmed processor for localization of the aorta and left atrium from magnetic resonance data, the storage medium comprising instructions for:
receiving the magnetic resonance data representing a patient;
jointly detecting the aorta and the left atrium from the magnetic resonance data; and
determining a location of the aorta and a location of the left atrium from the jointly detecting.

15. The non-transitory computer readable storage medium of claim 14 wherein receiving comprises acquiring with a localizer acquisition of pseudo-short axis views with a magnetic resonance scanner.

16. The non-transitory computer readable storage medium of claim 14 wherein jointly detecting comprises detecting a bounding box surrounding the aorta and the left atrium in two-dimensions and wherein determining comprises inferring the location of the aorta and the location of the left atrium from a position of the bounding box.

17. The non-transitory computer readable storage medium of claim 14 wherein jointly detecting comprises detecting the aorta and the left atrium in a two-dimensional plane as a single object.

18. A system for localization of the aorta and left atrium from magnetic resonance data, the system comprising:
a magnetic resonance scanner configured to acquire magnetic resonance data representing a three-dimensional region of a patient; and
a processor configured to detect a left ventricle in the three-dimensional region of the patient from the magnetic resonance data, to detect an object encompassing both the aorta and the left atrium based on the left ventricle, and to localize the aorta and the left atrium from the object.

19. The system of claim 18 wherein the processor is configured to detect a left ventricle base and a long axis direction of the left ventricle in the three-dimensional region, and to detect the object in a planar region positioned relative to the long axis direction and the left ventricle base.

20. The system of claim 18 wherein the magnetic resonance scanner comprises an iso-center and a moveable patient bed, and wherein the processor is configured to move the moveable patient bed to position the patient relative to the iso-center as a function of the localized aorta, localized left atrium, or both.

* * * * *